United States Patent [19]

Phillips

[11] Patent Number: 4,865,019

[45] Date of Patent: Sep. 12, 1989

[54] RETRACTOR APPARATUS FOR USE IN HARVESTING MAMMARY ARTERIES DURING HEART BY-PASS SURGERY

[76] Inventor: Steven J. Phillips, 5300 Woodland, Des Moines, Iowa 50312

[21] Appl. No.: 160,205

[22] Filed: Feb. 25, 1988

[51] Int. Cl.[4] .............................................. A61B 17/02
[52] U.S. Cl. ..................................................... 128/20
[58] Field of Search ........................... 128/20, 17, 346

[56] References Cited

U.S. PATENT DOCUMENTS

| | | | |
|---|---|---|---|
| 3,227,156 | 1/1966 | Gauthier | 128/20 |
| 4,617,916 | 10/1986 | LeVahn | 128/20 |
| 4,702,230 | 10/1987 | Pelta | 128/20 |
| 4,726,356 | 2/1988 | Santilli et al. | 128/20 |
| 4,797,394 | 5/1988 | Wantanabe | 128/20 |

FOREIGN PATENT DOCUMENTS

| | | | |
|---|---|---|---|
| 3717915 | 12/1987 | Fed. Rep. of Germany | 128/20 |
| 1019217 | 10/1952 | France | 128/20 |

OTHER PUBLICATIONS

A New Concept in Sternal Retraction: Applications for Internal Mammary Artery Dissection and Valve Replacement Surgery–Aurelio Chaus, M.D. and Carlos Blanche, M.D., The Annals of Thoracic Surgery, vol. 42, No. 4, Oct. 1986, pp. 73–74.
Internal Mammary Retractor–Rais A. Beg, M.D., H. Naraghipour, M.D., Earle B. Kay, M.D. and Phil Rullo, American Thoracic Surgery, vol. 39, No. 3, Mar. 1985, pp. 286–287.
Significant Improvement in Flow Through a Potential Internal Mammary Graft After Partial Approximation of te Sternum–Joseph E. Graham, M.D., Mohan Peter, M.D., and John Mathai, M.D., The Journal of Thoracic and Cardiovascular Surgery, vol. 88, No. 3, Sept. 1984, p. 454.
A New Self-Retaining Internal Mammary Artery Retractor–G. Campalani, M.D. and P. B. Deverall, F.R.C.S.–The Journal of Cardiovascular Surgery, vol. 28, No. 3, May-Jun., 1987, pp. 347–348.
Sternal Retractor for Improved Vision During Bilateral Internal Mammary Artery Implantation–Cedric Deal and Ian Monk, Thorax, vol. 24, No. 5, Sept., 1969, pp. 637–638.
Unilateral Self-Rataining Retractor for Use in Internal Mammary Artery Dissection–Rene G. Favaloro, M.D.–Journal of thoracic and Cardiovascular Surgery, vol. 53, No. 6, Jun., 1967, pp. 864–865.
A Modified Sternal Retractor for Explosure of the Internal Mammary Artery–Peter P. McKeon, M.B., B.S., John Crew, M.D., Elias S. Hanna, M.D., and Reinold Jones, M.D., Ann Thoracic Surgery, vol. 32, No. 6, Dec., 1981, p. 619.
Codman Cardiovascular & Thoracic Instruments, Codman & Schurtleff, Inc., 1976, brochure.
Problems of Major Chest Wall Reconstruction–Thaddeus E. Starzynski, M.D., Reuven K. Snyderman, M.D., and Edward J. Beattie, Jr., M.D., Plastic and Reconstructive Surgery, vol. 44, No. 6, Dec., 1969.

*Primary Examiner*—Edward M. Coven
*Assistant Examiner*—Mark S. Graham
*Attorney, Agent, or Firm*—Henderson & Sturm

[57] ABSTRACT

A retractor apparatus for use in harvesting mammary arteries during heart by-pass surgery including an elongated member having a first arm operably attached thereto which extends generally transversely to the elongated member. Structure is provided for attachment to the first arm member for holding one side of a cut in a patient's chest. A second arm member is disposed generally transversely with respect to the elongated member and includes a mechanism for movably attaching the second arm member to the elongated member so that the distance of the second arm member from the first arm member can be adjusted. Rake retractors are operably attached to the second bar for grasping the other side of a cut in the patient's chest. A counter pressure bar is adapted to be placed along, but spaced from the edge of the other side of the cut in the patient's chest and an adjusting mechanism is operably attached to the elongated member for adjusting the position of the counter pressure bar with respect to the elongated member whereby the other side of the cut in the patient's chest may be everted by using the attaching structure to move the rake retractor to pull the other edge of the cut up beside the counter pressure bar for thereby bringing the mammary artery into the visual field of a heart surgeon for harvesting. This structure is useful for harvesting both the right and the left mammary arteries.

3 Claims, 4 Drawing Sheets

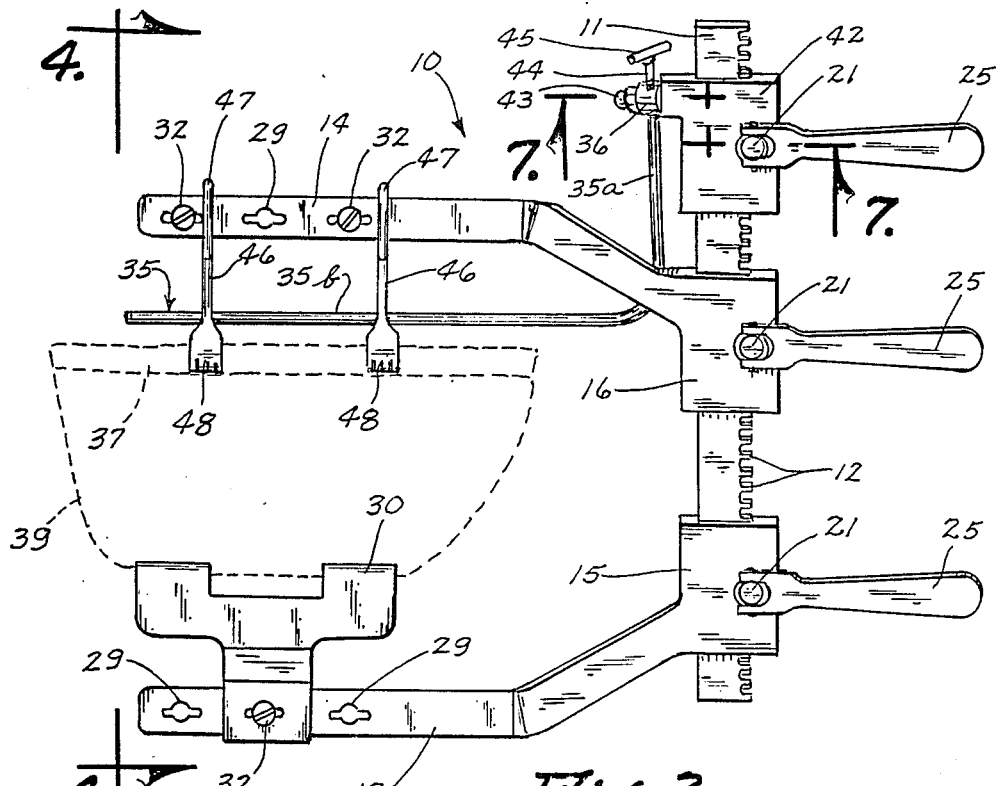
Fig. 3
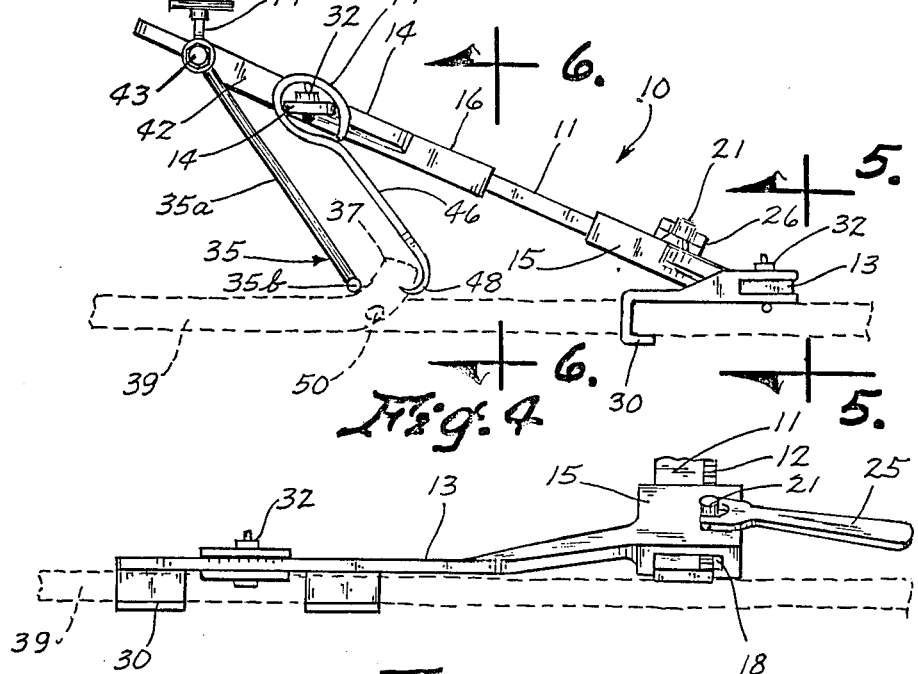
Fig. 4
Fig. 5

RETRACTOR APPARATUS FOR USE IN HARVESTING MAMMARY ARTERIES DURING HEART BY-PASS SURGERY

TECHNICAL FIELD

The present invention relates to a retractor apparatus for use in harvesting mammary arteries during heart by-pass surgery, and more particularly to such an apparatus having an adjustable counter pressure bar for facilitating the eversion of one edge of a chest cut for bringing a mammary artery into full view of a heart surgeon.

BACKGROUND ART

By-pass surgery is a well known procedure for replacing blood vessels clogged with cholesterol and fat in a human being with blood vessels which will cause blood to flow around the clogged vessels.

While many different blood vessels in the human body have been used as a by-pass blood vessel, preferred blood vessels to use are the left and right mammary artery.

After the chest and breast plate bone have been cut in preparation for facilitating access to the patient's heart during heart by-pass surgery, the left and right mammary artery will be just below the surface of each side of the cut in the chest. Since the portion of the chest adjacent to the cut is very stiff, it is impossible to manually evert the edge to facilitate easy harvesting of the mammary arteries. It is very difficult to harvest the mammary arteries without bringing them into full view by eversion of the edges of the cut in the chest. To date, there is no completely satisfactory apparatus for achieving the eversion of the edges, therefore there is a need for an apparatus which will quickly, easily and dependably accomplish this function so that the mammary arteries can be held in full view of the surgeon for the harvesting process.

DISCLOSURE OF THE INVENTION

The present invention relates to a retractor apparatus for use in harvesting mammary arteries during heart by-pass surgery. An elongated member has a first arm operably attached thereto which extends generally transversely to the elongated member. Structure is provided for attachment to the first arm member for holding one side of a cut in a patient's chest. A second arm member is disposed generally transversely with respect to the elongated member and includes a mechanism for movably attaching the second arm member to the elongated member so that the distance of the second arm member from the first arm member can be adjusted. Rake retractors are operably attached to the second bar for grasping the other side of a cut in the patient's chest. A counter pressure bar is adapted to be placed along, but spaced from the edge of the other side of the cut in the patient's chest and an adjusting mechanism is operably attached to the elongated member for adjusting the position of the counter pressure bar with respect to the elongated member whereby the other side of the cut in the patient's chest may be everted by using the attaching structure to move the rake retractors to pull the other edge of the cut up beside the counter pressure bar for thereby bringing the mammary artery into the visual field of a heart surgeon for harvesting. This structure is useful for harvesting both the right and the left mammary arteries.

An object of the present invention is to provide a retractor apparatus for use in harvesting mammary arteries during heart by-pass surgery.

Another object of the present invention is to provide a retractor apparatus of the aforementioned type which includes a counter pressure bar which is easily adjusted to facilitate easy and quick eversion of one edge of a cut in a patient's chest for exposing a mammary artery for harvesting by a heart surgeon.

Other objects, advantages, and novel features of the present invention will become apparent from the following detailed description of the invention when considered in conjunction with the accompanying drawings.

BRIEF DESCRIPTION OF THE DRAWINGS

FIG. 3 is an enlarged top plan view of the preferred view of the preferred embodiment shown in FIG. 1 in the process of everting one edge of the cut in a patient's chest during heart by-pass surgery;

FIG. 4 is a view taken along line 4—4 of FIG. 3;

FIG. 5 is a partial view taken along line 5—5 of FIG. 4;

BEST MODES FOR CARRYING OUT THE INVENTION

Figure 1:
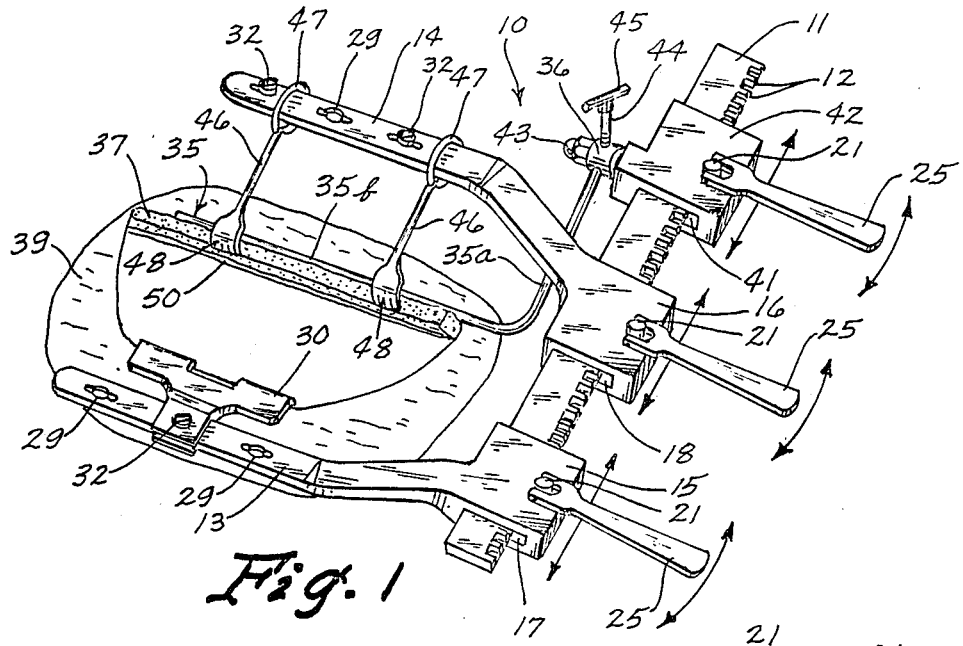
FIG. 1 is a perspective view of a preferred embodiment of the present invention shown during the process of everting one edge of a cut for exposing a mammary artery thereunder for use in heart by-pass surgery.

Referring now to the drawings wherein like reference numerals designate identical and corresponding parts throughout the several views, FIG. 1 shows a retractor apparatus (10) constructed in accordance with the present invention.

An elongated member (11) has rounded teeth (12) disposed along one edge thereof. A first arm member (13) and a second arm member (14) are movably attached to the elongated member (11) by connectors (15) and (16) having slots (17) and (18) therein and ratchet openings (19) and (20) respectively.

A ratchet member (21) has a pair of cylindrical posts (22) leading from a bottom portion (23) and a top portion (24). A handle (25) is pivotally connected to the ratchet (21) by a pin (26) which extends through an opening (27) in the ratchet (21) and through openings (28) in one end of the handle (25). Rotating the handles (25) in one direction causes movement of the arms (13) and (14) in one linear direction and rotation of the handles (25) in the opposite direction causes movement of the arms (13) and (14) in an opposite linear direction.

Openings (29) in the arms (13) and (14) are provided for attachment to sternal blades (30) whereby a fastener (32) extends down through openings (31) in the sternal blades and through the openings (29) and either of arms (13) and (14) whereupon rotation of the fastener (32) 90° locks the sternal blade (30) to the arm (13) or (14).

A counter pressure bar (35) is substantially L-shaped and has one leg (35a) which is welded to a collar (36) and another leg (35b) which is adapted to extend along but spaced from one edge (37) of a cut in a patient's chest (39). The collar (36) rotatably fits on a threaded post (40) which extends somewhat downwardly and rearwardly from the connector (42). The connector (42) is substantially like the connector (15) and therefore has an opening (41) and (49) just like openings (17 and 19) in the connector (15).

A threaded cap (43) prevents the collar (36) from coming off of the post (40) and a set screw (44), having an upper handle (45) thereon, is provided for extending through an opening (46) in collar (37) to engage the post (40) and thereby lock the collar and the arm (35) from rotation once it is adjusted to the position desired by the surgeon. Rake retractors (46) have a loop (47) on one end thereof and a curved fork-like structure (48) on the other end thereof for extending into and grasping the edge (37) of the cut in the chest (39).

In operation of the retractor apparatus (10) shown in FIGS. 1-8, it is noted that after the cut in the chest (39) has been accomplished, the sternal blade (30), having been attached to the arm (13), is utilized to hold the left edge (38) apart from the right edge (37). Rake retractors (46) are slipped onto the arm (14) through openings (47) therein and the sharpened lower portions (48) are hooked into the tissue in the edge (37) of the cut in the chest (39), for example as shown in FIGS. 1 and 4.

The position of the counter pressure bar (35) is then adjusted by loosening the set screw (44) and pivoting the arm (35) to the position desired, while at the same time moving the connector (42) laterally along the elongated member (11), so that the counter pressure arm (35) lies adjacent to but spaced from the edge (37). Once the counter pressure bar (35) is properly adjusted, the arm (14) can be moved away from the arm (13) by rotating the handle (25) on housing (16) in the proper direction to cause such movement of arm (14). This will cause the rake retractors (46) to pull the edge (37) up beside and possibly over the counter pressure bar (35) as shown in FIG. 1 thereby exposing the mammary artery (50) and making the mammary artery (50) come into the full view of the surgeon. The surgeon can then harvest the mammary artery (50) in a conventional fashion for use in bypassing clogged arteries in the patient's heart.

Figure 8:
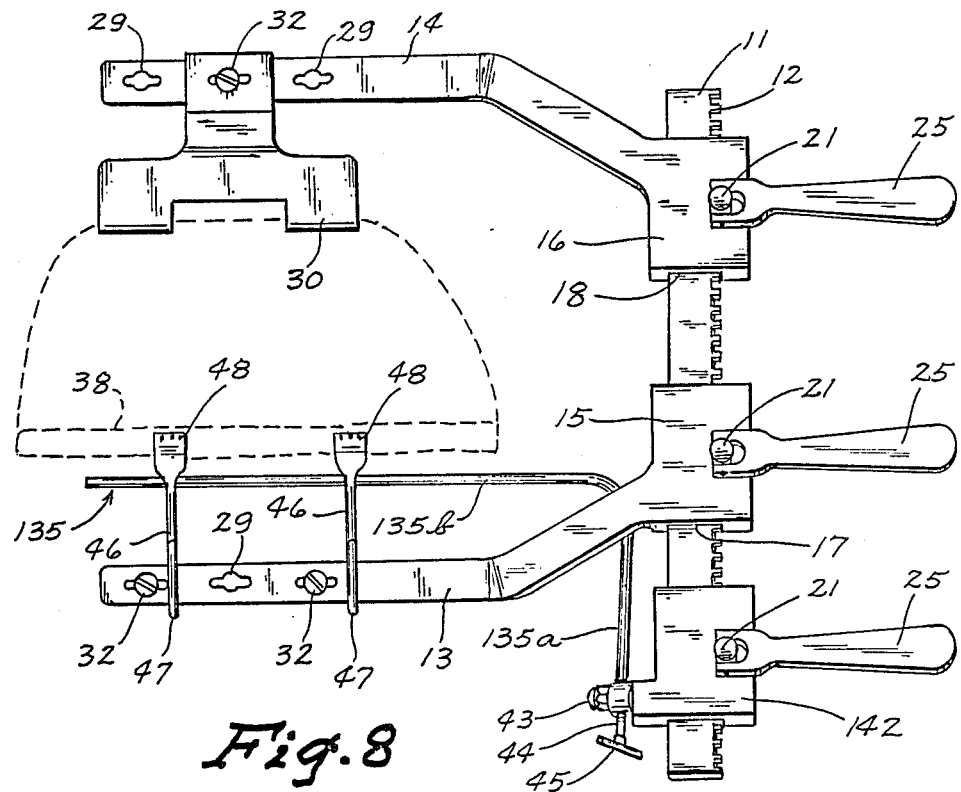
FIG. 8 is a view like FIG. 3 but showing an additional counter pressure bar and adjusting mechanism therefore for everting the other side of the cut in the patient's chest for everting such other side of the cut.

To harvest the mammary artery underneath the edge (38) of the cut in the patient's chest (39), the arrangement in FIG. 8 is used wherein a separate and different counter pressure bar (135) is disposed on the other end of the elongated member (11) and is movable therealong. The sternal blade (30) is connected to the arm (14), instead of the arm (13), and the rake retractors (46) are connected to the arm (13) as shown in FIG. 8. The procedure is then a mirror of what was explained above for harvesting the mammary artery (50). The counter pressure bar (135) is rotated into a proper position after loosening the set screw (44) and then tightened down when counter pressure bar (135) is in a proper rotary position. Counter pressure bar (135) is moved laterally along the elongated member (11) by rotation of the handle (25) in a proper rotary direction. Once in a proper position, the arm (13) would be moved away from the arm (14) by rotation of the handle (25) extending through member (15) to evert the edge (38) and harvest a mammary artery disposed thereunder.

Figures 6, 7, 9:
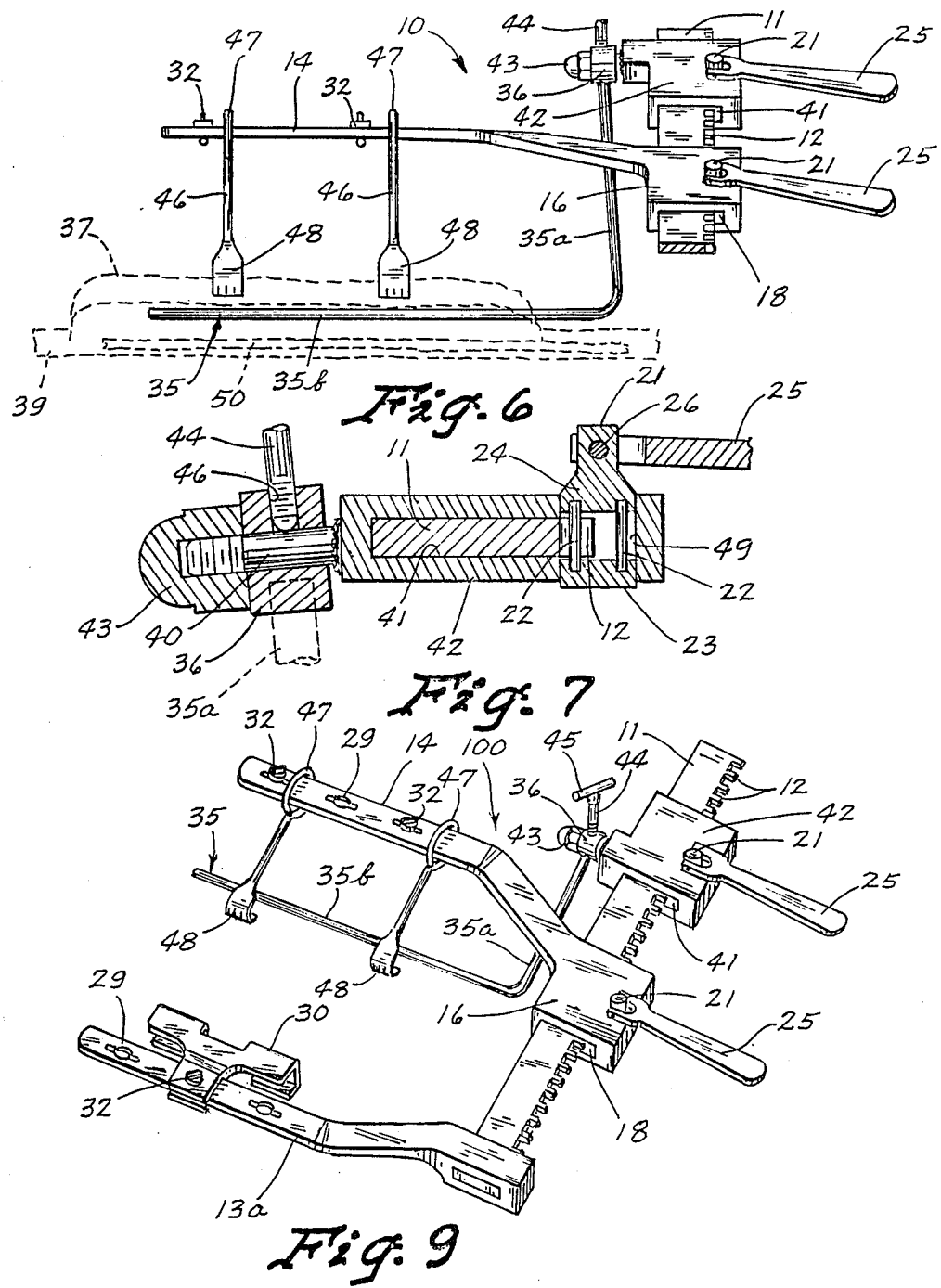
FIG. 6 is a cross sectional view taken along line 6—6 of FIG. 4.
FIG. 7 is an enlarged cross sectional view taken along line 7—7 of FIG. 3.
FIG. 9 is a perspective view of an alternate form of the invention which has one arm permanently affixed to one end of an elongated ratchet member and another arm movably attached thereto.

Referring now to FIG. 9, an alternate form of the invention (100) is shown which is substantially identical to that shown in embodiment (10) of FIG. 1 except that an arm (13a) is connected permanently, such as by welding, to one end of the elongated member (11). The operation for harvesting a mammary artery is exactly the same as described above with respect to the left mammary artery (50) as shown in FIG. 1, but when the right mammary artery under the cut (38) of the chest (39) is to be harvested, the entire apparatus (100) is turned around 180° so that the arms (13a) and (14) extend in the opposite direction from that shown in FIG. 9 whereupon the sternal blade (30) can be attached under and around the patient's left edge cut (37) and the rake members (46) can attach to the edge (38) of the chest (39) and whereupon the elongated member (11) will be closer to the patient's head than for harvesting the mammary artery under edge (38) than it will be when used to harvest the mammary artery (50) under the edge (37).

Figure 2:
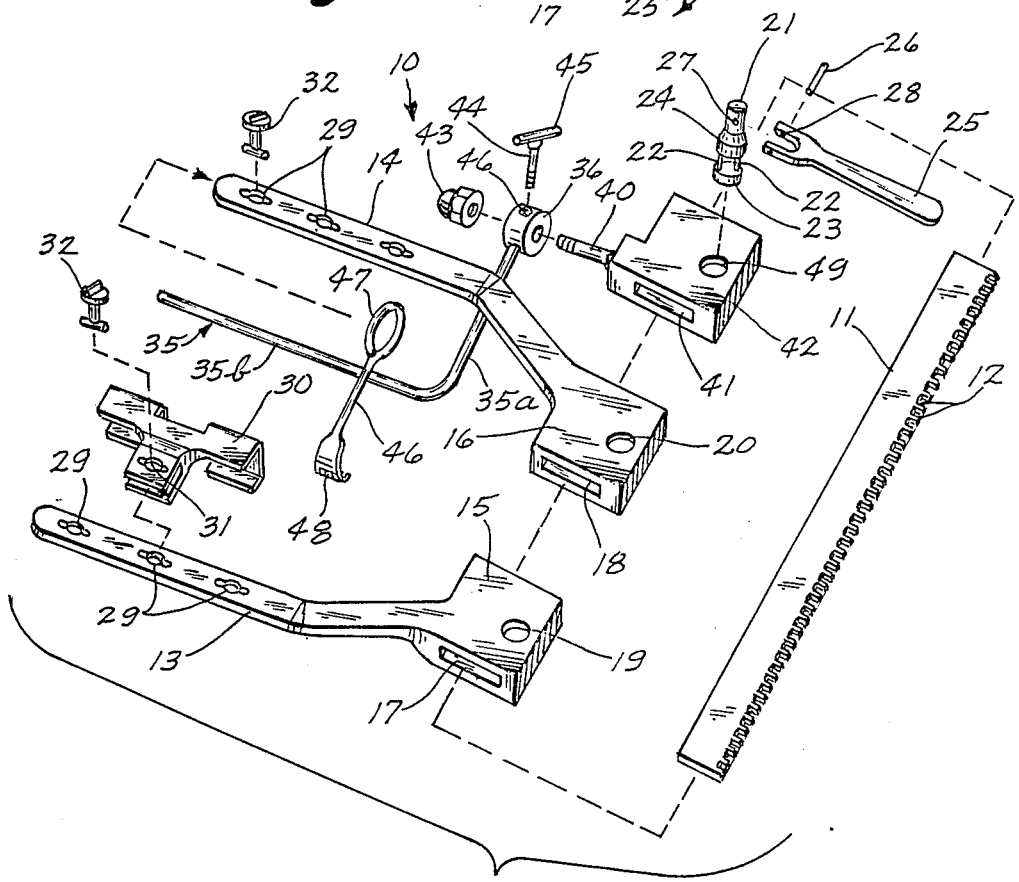
FIG. 2 is a perspective exploded view of the preferred embodiment shown in FIG. 1.

It is also noted that the longitudinal axis of the arm (35b) of counter pressure bar (35) is preferably parallel to the axis of the threaded post (40) shown in FIG. 2. In general, it is desirable that the axis of the counter pressure bar leg (35b) be generally parallel to the arm (14) and that the axis of the counter pressure bar (135) be generally parallel to the straight portion of the arm (13).

Accordingly, it will be appreciated that the preferred embodiments (10) and (100) disclosed herein do indeed accomplish the aforementioned objects. Obviously, many modifications and variations of the present invention are possible in light of the above teachings. It is therefore to be understood that, within the scope of the appended claims, the invention may be practiced otherwise than as specifically described.

I claim:

1. A retractor apparatus for use in harvesting a mammary artery in heart by-pass surgery, comprising:
   an elongated member;
   a first arm member operably attached to said elongated member and extending generally transversely with respect to said elongated member;
   means operably attached to said first arm member for holding one side of a cut in a patient's chest;
   a second arm member disposed generally transversely with respect to said elongated member;
   means for movably attaching said second arm member to said elongated member so that the distance of said second arm member from said first arm member can be adjusted;
   rake retractor means operably attached to said second arm member for grasping the other side of of a cut in the patient's chest, said rake retractor means being substantially longer than said holding means;
   a counter pressure bar adapted to be placed along but spaced from the edge of the other side of the cut in the patient's chest; and
   adjusting means operably attached to said elongated member for adjusting the position of said counter pressure bar with respect to said elongated member whereby said other side of the cut in a patient's chest may be everted by using the attaching means to move the rake retractors to thereby pull the edge of the other side of the cut up beside the counter pressure bar for thereby bringing the mammary artery under the cut into the visual field of a heart surgeon, said adjusting means including a first means for pivoting said counter pressure bar about a first axis and a second means for adjusting the position of said first means along said elongated member, said counter pressure bar being somewhat L-shaped with one leg thereof having one end thereof connected to said pivoting means, the other end of said one leg being connected to the other leg of the L-shaped counter pressure bar, the longitudinal axis of the other leg being substantially parallel to said first axis.

2. The apparatus of claim 1 including means for adjusting the position of said first arm member with respect to said elongated member.

3. The apparatus of claim 1 wherein said second arm member has a longitudinal axis and the longitudinal axis of said second arm is generally parallel to the longitudinal axis of the other leg of said counter pressure bar.

* * * * *